United States Patent [19]

Quaglia

[11] 4,182,630
[45] Jan. 8, 1980

[54] PIVALYL-ACETANILIDE COUPLERS AND PHOTOGRAPHIC ELEMENTS INCLUDING THEM

[75] Inventor: Andrea Quaglia, Albisola Mare, Italy

[73] Assignee: Minnesota Mining and Manufacturing Company, St. Paul, Minn.

[21] Appl. No.: 589,527

[22] Filed: Jun. 23, 1975

[30] Foreign Application Priority Data

Jun. 26, 1974 [IT] Italy ............................... 51757 A/74

[51] Int. Cl.$^2$ ............................ G03C 1/40; G03C 7/00
[52] U.S. Cl. ..................................... 430/558; 430/389; 430/226
[58] Field of Search ............... 96/100, 74, 56.5, 77, 96/56.2, 66.3; 260/308 R

[56] References Cited

U.S. PATENT DOCUMENTS

| 2,444,608 | 7/1948 | Heimbach et al. | 96/109 |
|---|---|---|---|
| 3,148,062 | 9/1964 | Whitmore et al. | 96/100 |
| 3,458,315 | 7/1969 | Loria | 96/56.2 |
| 3,617,291 | 11/1971 | Sawdey | 96/56.5 |
| 3,770,436 | 11/1973 | Fujiwhara et al. | 96/56.5 |
| 3,900,483 | 8/1975 | Fjuimatsu et al. | 96/100 |
| 3,930,863 | 1/1976 | Shiba et al. | 96/74 |
| 3,933,500 | 1/1976 | Shiba et al. | 96/56.5 |
| 4,049,458 | 9/1977 | Boie et al. | 96/100 |

FOREIGN PATENT DOCUMENTS 2433812   6/1975   Fed. Rep. of Germany ............. 96/100

*Primary Examiner*—Richard L. Schilling
*Attorney, Agent, or Firm*—Cruzan Alexander; Donald M. Sell; Mark A. Litman

[57] ABSTRACT

Two-equivalent pivalylacetanilide couplers having attached to the reactive methylene thereof a 5-membered (simple) or 6-membered (simple or condensed) heterocyclic nucleus through nitrogen atoms respectively in 1 position and 3 position thereof, said 5-membered nucleus including nitrogen atoms in 2 and 4 positions respectively bonded through double bonds to carbon atoms in 3 and 5 positions thereof and said 6-membered heterocyclic nucleus being chosen within the class including 1,2,3-benzotriazine-4-(3H)-one, 1,3-benzodiazine-4-(3H)-one and pyrimidine-4-(3H)-one nucleus.

8 Claims, No Drawings

PIVALYL-ACETANILIDE COUPLERS AND PHOTOGRAPHIC ELEMENTS INCLUDING THEM

A multilayer photographic element for use in col or photography normally includes at least three silver halide emulsion layers which are sensitive to the blue, green and red regions of the visible spectrum and respectively contain yellow, magenta and cyan forming couplers associated therewith in the same or adjacent layers which have to be chosen to form balanced color images.

Sometimes the couplers are not included in the photographic element but are included in development bath (bath couplers) which includes the p-phenylene diamine color developer.

In any case, the couplers have to react with the p-phenylene diamine compound to form a dye which is either yellow, magenta or cyan as per above in the presence of reactive silver halide (that is silver halide exposed to the light or fogged as known in the art).

Particularly, a yellow coupler does include a reactive methylene while the p-phenylene diamine compound includes a $NH_2$ group which upon coupling reaction reacts with said methylene to form a carbon-nitrogen double bond in the presence of four reactive silver ions (present in the form of silver halide). If a hydrogen atom is substituted with a suitable splitting off substituent, the coupler (which is called in the art "two-equivalent coupler") requires only two exposed silver ions to give the same coupling reaction with the p-phenylene diamine compound.

Hence the major advantage of yellow forming two-equivalent couplers: they require less silver than normal four-equivalent couplers to give the same amount of dye, that is the same optical density. Their cost however is generally higher with respect to four-equivalent couplers because of the presence of the splitting off group which may require difficult and expensive chemical reactions to be attached to the reactive methylene.

It is generally worthwhile using two-equivalent couplers when they are very reactive in a way as to have a silver saving higher than additional expenses for their preparation.

In the case of pivalylacetanilide couplers, the problem of having good two-equivalent couplers has been broadely investigated (see for example U.S. Pat. Nos. 3,265,506; 3,384,657; 3,408,194; 3,644,498; 3,730,722; DT 2,163,812; 2,213,461; 2,261,361; 2,318,807; FR 2,134,506; BE 782,605; 793,446), not only because of economical reasons but also because of technical reasons mainly annected to the fact that four-equivalent pivalylacetanilide couplers form very pure dyes upon reaction with p-phenylene diamine compounds in the presence of reactive silver ions but are poorly reactive in a way as not to have any practical importance.

The known two-equivalent pivalylacetanilide couplers have some drawbacks connected to their reactivity (it is too high with a non-wanted "stain", that is a color density in non exposure areas or it is too low) and/or to their physical properties (above all their solubility in organic solvents when the couplers are to be used with the dispersion technique as later described) and/or to their stability at the various temperature, light and humidity conditions and/or to the stability of the dyes derived therefrom (upon color development with the p-phenylene diamine compounds) which form the photographic images in the processed silver halide photographic element.

I have now found a new class of two-equivalent pivalylacetanilide compounds which have a very good reactivity and do not show any of the above drawbacks or do show them at a very limited extent.

The compounds of my invention can be generally described as two-equivalent pivalylacetanilide couplers having attached to the reactive methylene thereof a 5-membered (simple) or 6-membered (simple or condensed) heterocyclic nucleus through nitrogen atoms respectively in 1-position and 3-position thereof, said 5-membered nucleus including nitrogen atoms in 2 and 4-positions respectively bonded through double bonds to carbon atoms in 3 and 5 positions thereof and said 6-membered heterocyclic nucleus (simple or condensed) being chosen within the class including 1,2,3-benzotriazine-4-(3H)-one, 1,3-benzodiazine-4-(3H)-one and pyrimidine-4-(3H)-one nucleus.

Said splitting off heterocyclic nucleus can be represented by the following formulas:

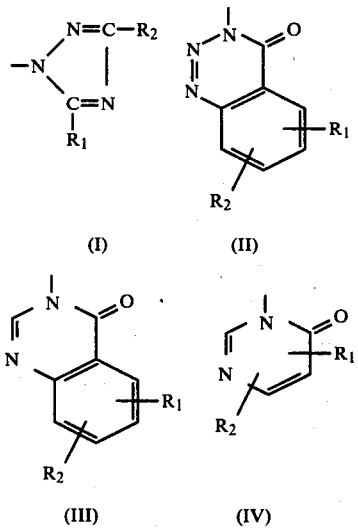

wherein $R_1$ and $R_2$ each represent a hydrogen atom or a substituent chosen within the class of halogen such as chlorine, bromine, iodine and fluorine, preferably chlorine and bromine; a carboxy acid ester whose alkyl chain has from 1 to 18 carbon atoms, preferably from 1 to 5; a substituted or not substituted amino group such as amine or phenylamine; a nitrogen containing heterocyclic nucleus such as for example a morpholine group attached through said nitrogen atom (we will call 1-nitrogen); an alkyl group having from 1 to 18 carbon atoms, preferably from 1 to 5; an alkylthio or alkoxy group having from 1 to 18 carbon atoms; preferably from 1 to 5; an alkylsulphoxy group having from 1 to 18 carbon atoms, preferably from 1 to 5; a carboxy acid group; a sulphoxy acid group; a non substituted phenyl group or a phenyl group substituted with substituents chosen within the class consisting of halogen, as for example chlorine, bromine, fluorine and iodine, alkyl having from 1 to 18 carbon atoms, preferably from 1 to 5; carboxy acid ester whose alkyl chain contains from 1 to 18 carbon atoms, preferably from 1 to 5, a cyan group, an alkoxy group including an alkyl group having from 1 to 18 carbon atoms, preferably from 1 to 5, a carboxy acid group, a sulphoxy acid group.

The above substituents are preferably attached only to the 3-position of the 5-membered splitting off nucleus represented by formula (I). The same substituents are preferably attached to the 5, 6, 7 and 8 positions of the 6-membered splitting off nucleus represented by formulas (II), (III) and (IV), more preferably to the 8-position and most preferably to the 6 and 8 positions thereof. Their presence and nature may simply depend upon preparation needs but can also be chosen for the purposes of reaching certain specific results as known to those skilled in the art. In any case they have to be reasonable in size and nature as not to negatively affect the properties of the obtained couplers.

It could be useful for example to have said substituents capable of imparting non diffusing properties to the coupler molecule which would otherwise be a diffusing one. This for example for the purposes of having a non diffusing coupler molecule which upon color development with a p-phenylene diamine compound forms a diffusible dye in the presence of an oxidant (as for example silver halide ions fogged or exposed to the light). Groups of this type are aliphatic chains, for example alkyl chains, having a total of at least 10 carbon atoms.

Hydrophilic solubilizing groups of sulphoxy and carboxy acid type can be introduced into the heterocyclic splitting off nucleus in combination with long alkyl chains attached to the acetanilide moiety of the coupler molecule for the purposes of having non diffusing couplers soluble in aqueous alkaline solutions (Fischer technique), as known to those skilled in the art. These groups, however, do generally raise the cost of preparation of the products and are to be avoided at least in this part of the molecule. They are of course to be avoided when the couplers are to be used with the dispersion technique because, in this case, the coupler molecule is to be a hydrophobic one. Acid ester groups can be usefully attached to the same splitting off nucleus to get better solubility in solvents used according to the solvent dispersion technique for introducing non diffusing couplers into gelatin layers as described in U.S. Pat. No. 2,322,027; 2,801,170; 2,801,171 and 2,991,177. (Briefly, the solvent dispersion technique involves first dissolving a coupler in a substantially water-immiscible organic solvent and then dispersing the so-prepared solution as extremely fine droplets in a hydrophilic colloidal binder. Gelatin is the preferred hydrophilic colloidal binder but other polymeric colloidal binder materials known to the art can also be used. Obviously, when the couplers are incorporated into the emulsion by the solvent dispersion technique, the dyes deriving therefrom upon color development are also contained dispersed in the emulsion dissolved in the substantially water-immiscible organic solvent). Also halogen, preferably chlorine and bromine, and other substituents, as for example alkylthio-group and morpholine group, attached to the 3-position of the 5-membered heterocyclic splitting off nucleus of the present invention, proved to raise the solubility of the coupler molecule in solvents useful within the dispersion technique.

Analogously halogen atoms, preferably chlorine and bromine, attached to the various positions, preferably to the 6 and/or 8-positions, of the 6-membered heterocyclic splitting off nucleus of the present invention, proved to improve the solubility and the reactivity of the pivalylacetanilide couplers including said nucleus, especially in the case of a benzotriazine-4-one nucleus when the coupler is used according to the above described dispersion technique.

Hence the preferred pivalylacetanilide couplers of the present invention are those containing a 1,2,4-triazole or a 1,2,3-benzotriazine-4-(3H)-one splitting off nucleus.

Thus the present invention refers to pivalylacetanilide couplers having attached to the reactive methylene thereof one heterocyclic splitting off group as above described and to a photographic element including a support base and at least one silver halide layer including a pivalylacetanilide coupler of the present invention associated with a silver halide emulsion. The present invention further refers to a method for forming a yellow colored dye in a photographic element including a support base and at least one silver halide emulsion layer by reaction of a p-phenylene diamine color developer and a yellow forming pivalylacetanilide coupler as described above. The present invention further refers to an exposed and processed photographic element including a yellow dye image formed upon color coupling reaction of a color pivalylacetanilide coupler of the present invention with a p-phenylene diamine compound.

Particularly, the present invention refers to non diffusing pivalylacetanilide couplers including aliphatic chains having a total of at least 10 carbon atoms attached to the acetanilide moiety thereof and to gelatin silver halide photographic elements including them dissolved in an organic solvent dispersed in the gelatin silver halide emulsion layer.

The acetanilide moiety of the pivalylacetanilide couplers of the present invention may have attached thereto every substituent known to the art provided it is chosen reasonable in size and nature depending on the use the coupler is made for (Fischer technique, solvent dispersion technique, diffusion transfer technique, bath technique and so on).

As said before, groups useful to be attached to the acetanilide moiety of the couplers of the present invention are aliphatic chains such as alkyl chains having a total of from 10 to 18 carbon atoms when the couplers are to be used with the solvent dispersion technique or solubilizing group such as sulphoxy and carboxy groups. These groups are generally attached to ortho, meta and para positions of the phenyl ring through link groups such as amine, carbonyl, alkylene, sulphonyl, oxygen, sulphur, phenyl and combinations thereof such as for example phenyloxy, phenyl oxyalkylene, carbonylamine (carbamyl), aminecarbonyl, sulphonylamine (sulphamyl), aminesulphonyl, oxyalkylenecarbonyl amine, oxyalkyleneaminecarbonyl, oxyalkylenesulphonylamine, oxyalkylaminesulphonyl, phenyloxyalkylenecarbonylamine, phenyloxyalkyleneaminecarbonyl, phenyloxyalkylenesulphonyl amine, phenyloxyalkylenesulphonylamine, phenyloxyalkyleneaminesulphonyl, the alkylene thereof, alkyl substituted or not having no more than a total of 7 carbon atoms.

The above groups are preferably attached to the 5 position of the aniline residue (relative to the amine group).

In this position, groups including alkyl groups and/or phenylene groups and/or oxygen and/or alkylene groups, amine and carbonyl groups (directly bonded together as to form a carbonylamine group or an aminecarbonyl group) cause the dye absorption λ max to be lower with respect to the same groups including amine and sulphonyl groups (directly bonded as to form a sulphonylamine or an aminesulphonyl group).

Associated with groups of the above type in 5 position of the aniline residue substituents of halogen type such as chlorine, bromine, iodine and fluorine, or alkoxy groups, dialkylamine groups and alkyl groups, preferably having no more than 18 carbon atoms, more preferably no more than five, are attached to the 2 position of the aniline residue itself.

A halogen group usually increases the oil solubility. A chlorine atom causes the dye absorption λ max to shift towards higher values (the fluorine has a similar but weaker effect), while an alkoxy group, for example a methoxy group, shifts the dye absorption λ max towards lower values.

Hence, various substituents can be attached both to the aniline residue and to the heterocyclic nucleus of the pivalylacetanilide couplers of the present invention as per the previous description. It is generally accepted in the art, however, that these groups should not be too heavy. An upper limit to their total weight would reasonably be 900. These upper limits have been indicated by assuming 25 as upper limit to the total number of carbon atoms present in alkyl chains of both acetanilide moiety and splitting off heterocyclic nucleus of the pivalylacetanilide couplers of the present invention.

Examples of couplers according to the present invention are the following numbered ones, while the couplers indicated with a letter are prior-art couplers.

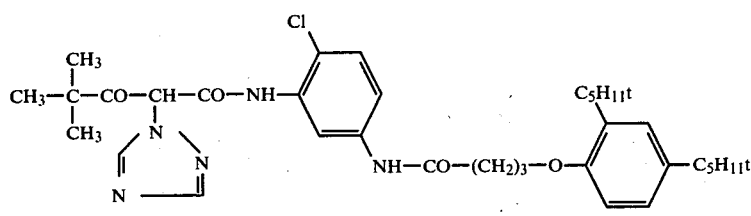

1.

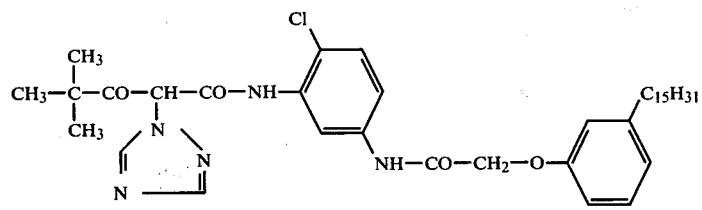

2.

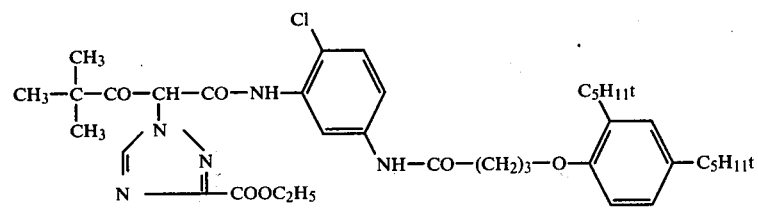

3.

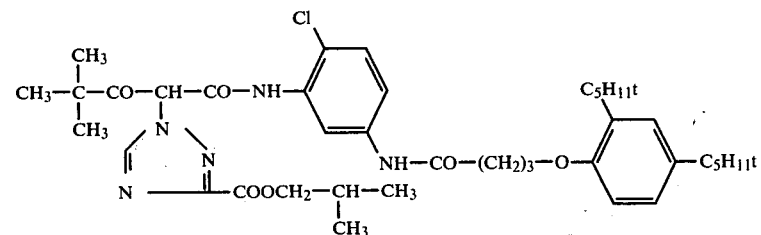

4.

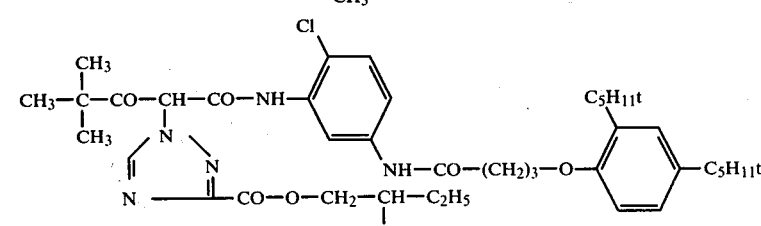

5.

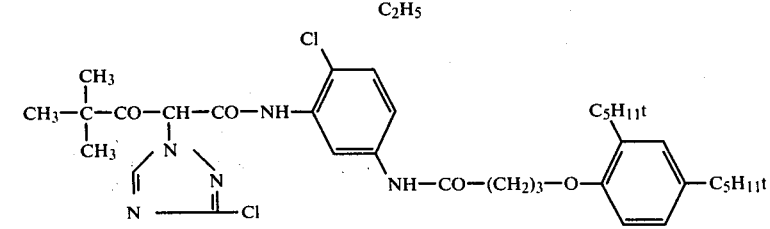

6.

-continued
7.
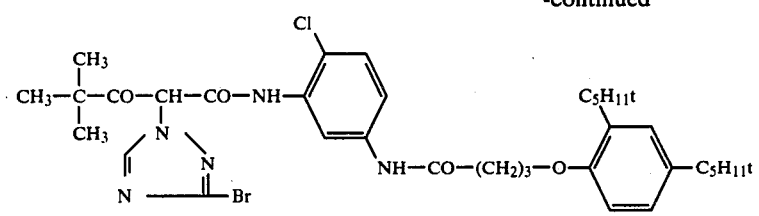
8.
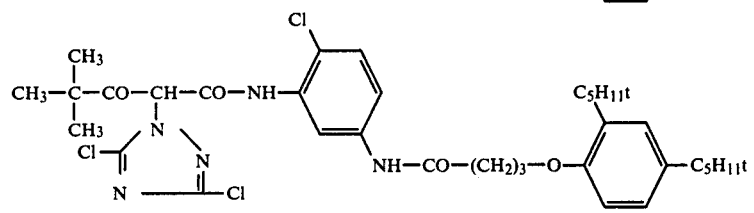
9.
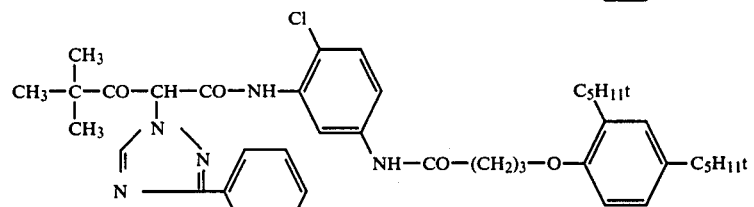
10.
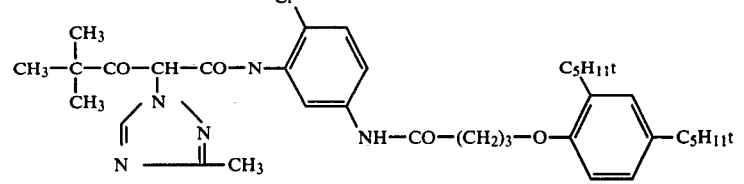
11.
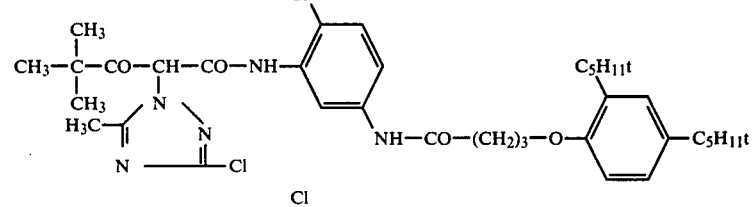
12.
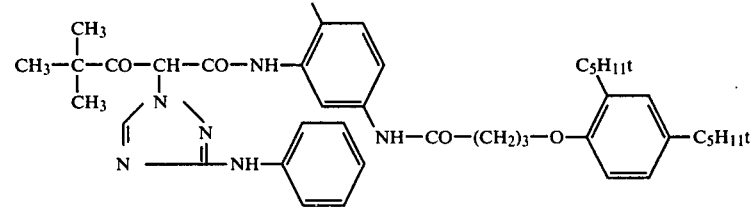
13.
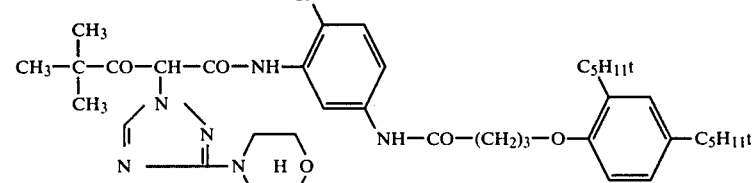
14.
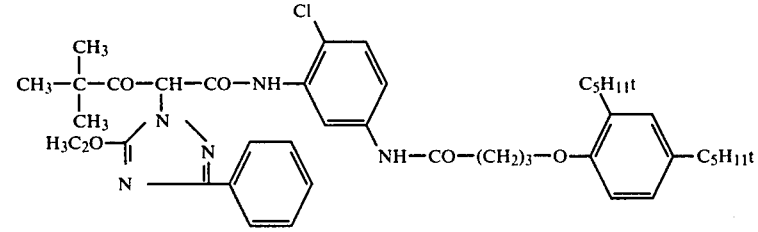

15. 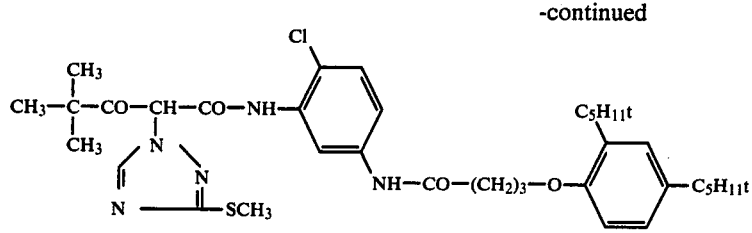
16. 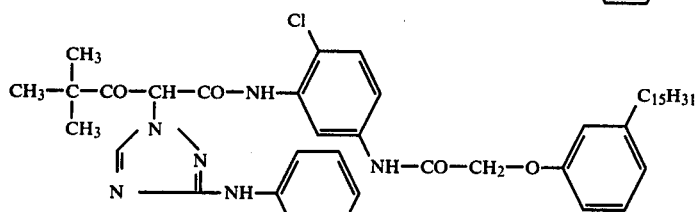
17. 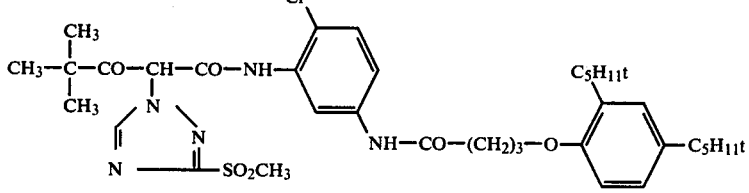
18. 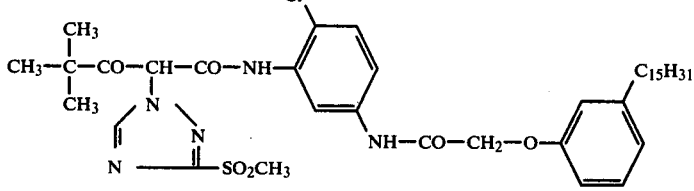
19. 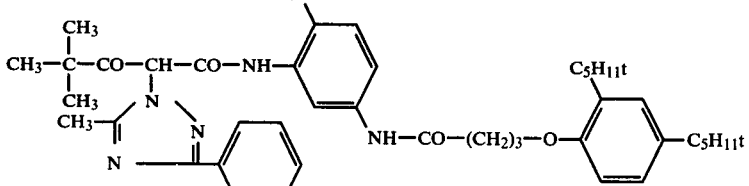
20. 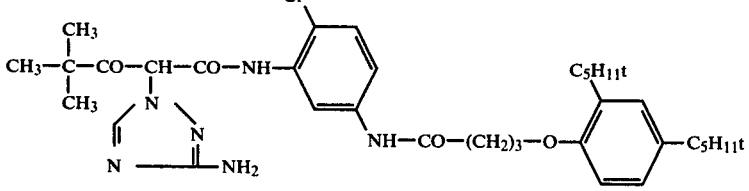
21. 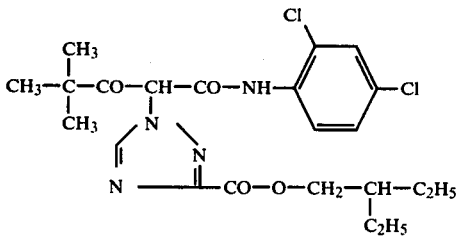
22. 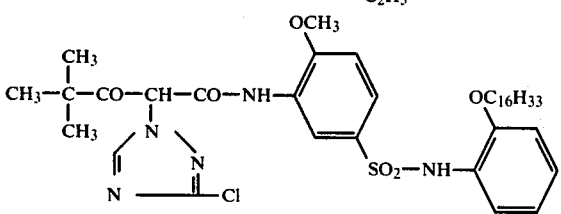

23. 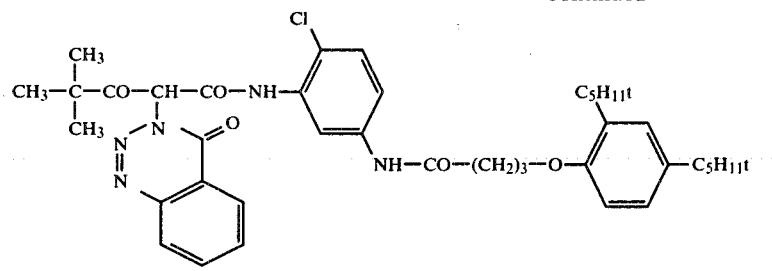
24. 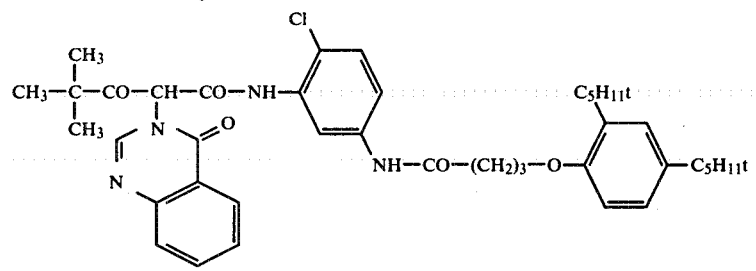
25. 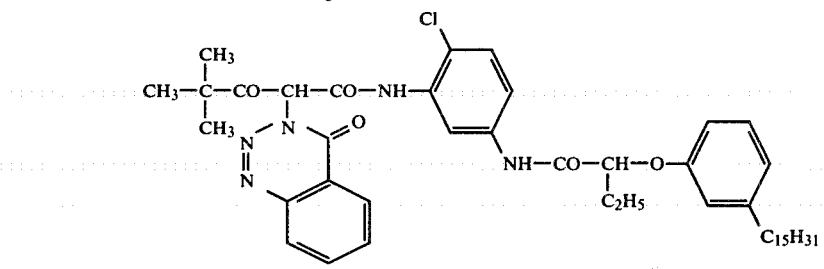
26. 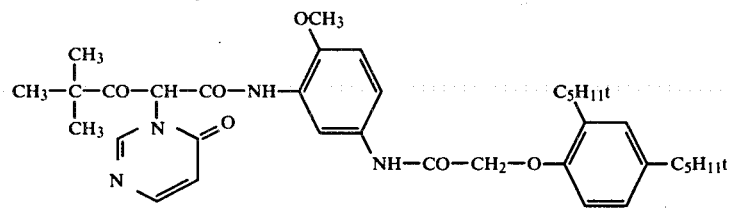
27. 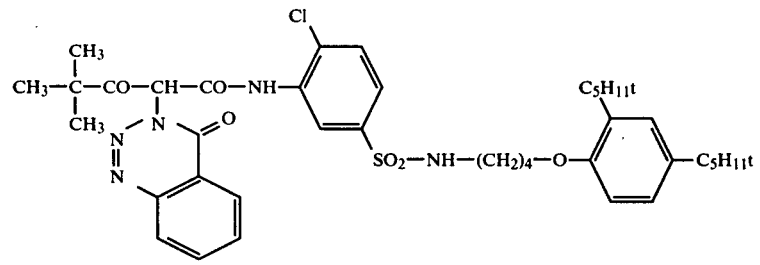
28. 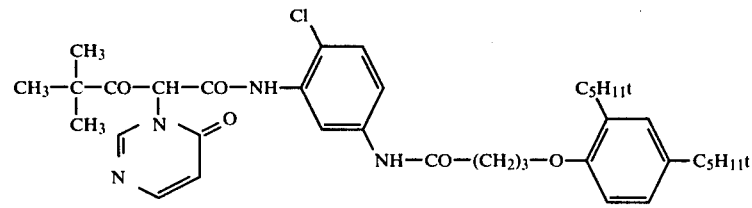
29. 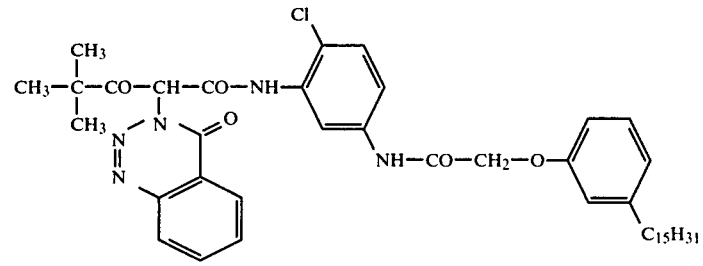

-continued
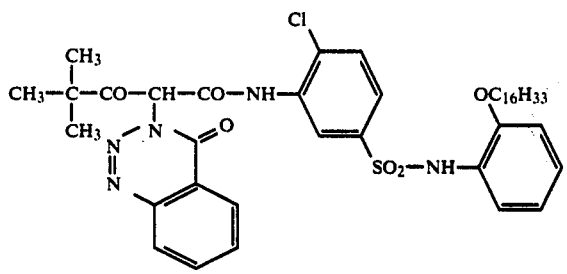
30.
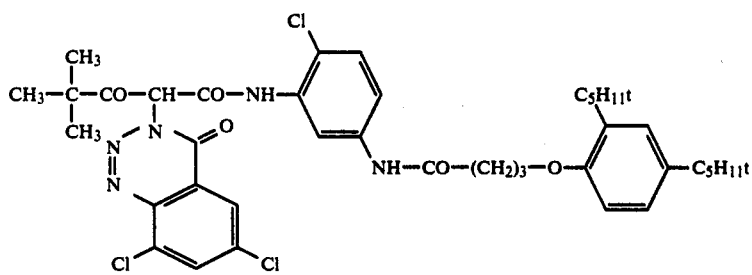
31.
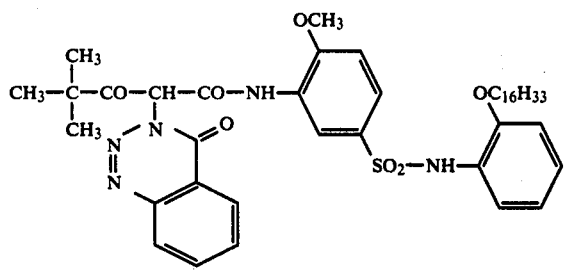
32.
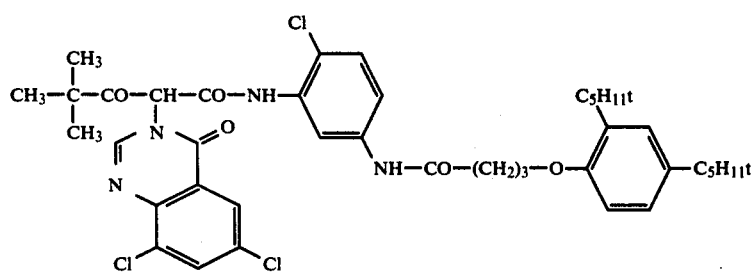
33.
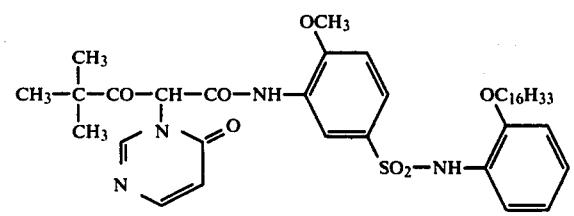
34.
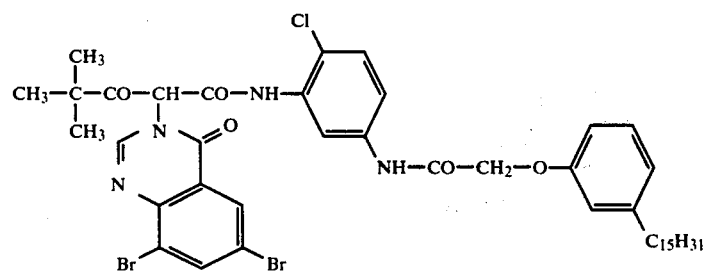
35.

-continued
36.
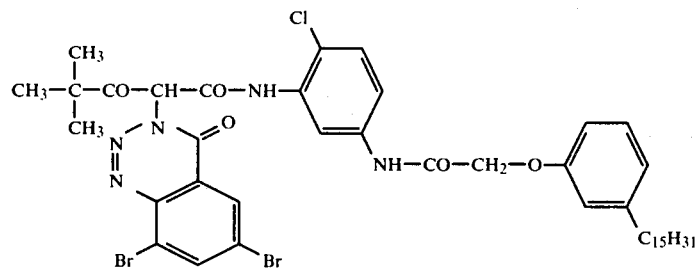
37.
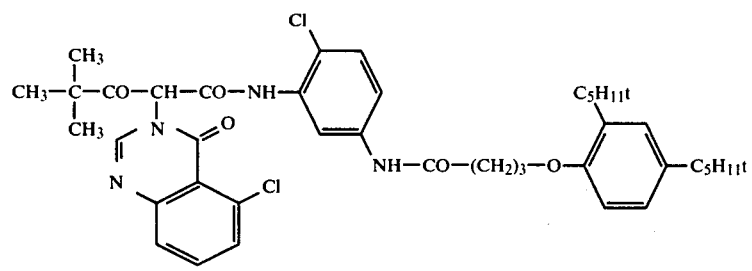
38.
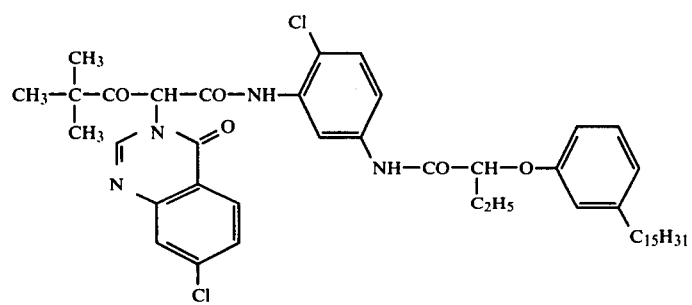
39.
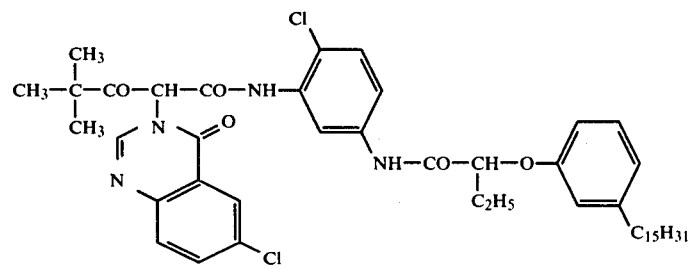
40.
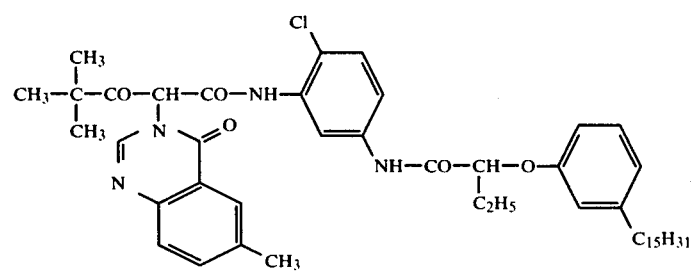
41.
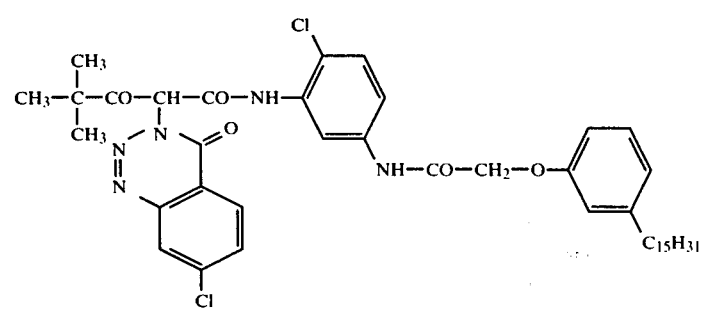

-continued

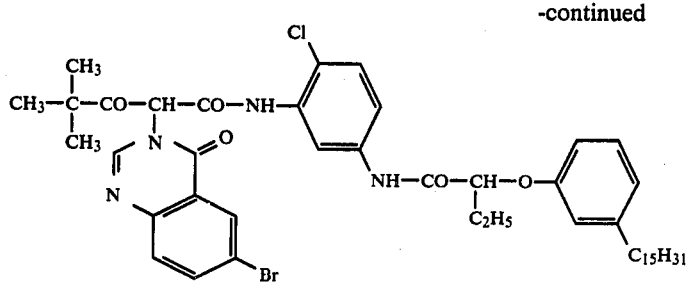

42.

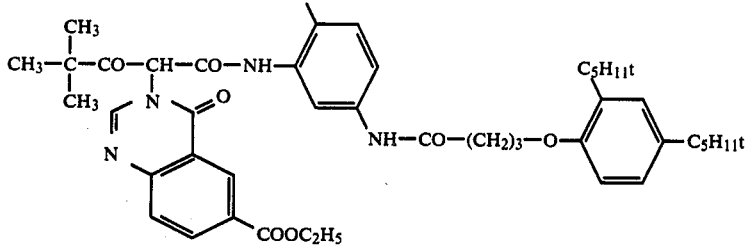

43.

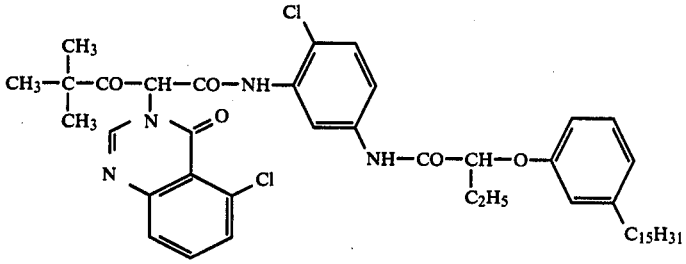

44.

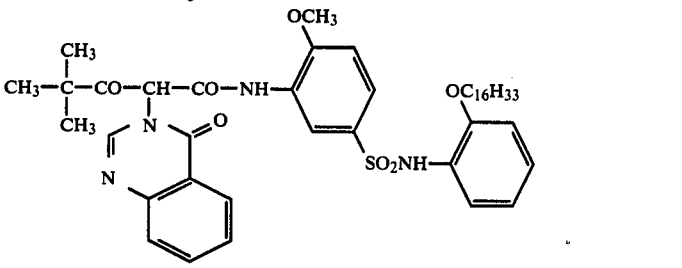

45.

The couplers of the present invention may be used in association with many types of silver halide emulsions suitable for color photography. They can be used for instance with silver bromide, silver chloride or silver iodide emulsions or with those emulsions containing a halide mixture, such as silver bromo-iodide or silver chloro-bromide emulsions. The couplers can also be used with those emulsions which are described in U.S. Pat. Nos. 2,592,243 and 2,698,794. Such couplers can still be used with those emulsions capable of forming an image on the surface or in the interior of the silver halide grains, such as those described in U.S. Pat. No. 2,592,250.

When the couplers of the present invention are included in photographic elements prior to their exposure and development, they can be directly introduced into the emulsions before their coating on photographic base or into a layer adjacent thereto.

As it is known to the man skilled in the art, the above mentioned emulsions can be chemically sensitized either by addition of sulfur compounds, as described for instance in U.S. Pat. Nos. 1,574,944; 1,623,469; 2,410,689; and by addition of noble metal salts, such as rhutenium, rhodium, iridium, palladium and platinum. Such emulsions can be chemically sensitized by addition of Au salts, as described in U.S. Pat. No. 2,399,083. They can be stabilized with Au salts as described in U.S. Pat. Nos. 2,597,856 and 2,587,915. The above mentioned emulsions can be optically sensitized with apomerocyanine dyes as those described in DT No. 1,009,020; GB No. 734,792; FR Nos. 1,559,295 and 2,018,196; U.S. Pat. Nos. 3,574,631 and in BE Nos. 746,342 and 747,781.

The emulsions can contain organic stabilizers and antifoggants of the cyclic amine type; iminoazoles such as mercapto-benzimidazole; triazoles such as those described in U.S. Pat. No. 2,444,608; azaindenes such as those described in U.S. Pat. Nos. 2,444,605; 2,444,606; 2,444,609; 2,450,397; 2,713,541; 2,716,062; 2,735,769; 2,743,181; 2,756,147; 2,772,164 and in E. J. Birr, Z. Wiss. Phot. 472 (1952); tetrazoles such as 1-phenyl-5-mercapto-tetrazole; thiazoles and benzothiazoles such as 1-methyl-benzothiazole and benzothiazole quaternary salts, as described in U.S. Pat. No. 2,131,038; mercapto-benzothiazoles such as 1-methyl-mercapto-benzo-thiazole; oxazoles, thiosemicarbazydes; pyrimidines; iodonium derivatives; benzenesulphynic acids; inorganic stabilizers of the zinc and cadmium salt type such as those described in U.S. Pat. No. 2,839,405.

The emulsions can further contain any suitable plasticizer known to the man skilled in the art such as glycerin.

The emulsion may be hardened with any suitable hardener for gelatin, known to the man skilled in the art such as aldehyde of the formaldehyde, glyoxale, succinic, glutaric and resorcylic aldehyde type; and halogen substituted aliphatic acids such as mucochloric and mucobromic acids as described in U.S. Pat. No. 2,080,019; or mixture thereof as described in U.S. Pat. No. 2,591,542.

The emulsions may have been supplied with a coating aid, known to the man skilled in the art such as saponin. Any suitable base type, known to the man skilled in the art, can be used, such as cellulose triacetate, polyester, paper, polytenated paper. In the preparation of the silver halide dispersions, employed for preparing silver halide emulsions, there may be employed as the dispersing agent for the silver halide in its preparation, gelatin or another water-permeable means of the colloidal albumin type, a cellulose derivative, or a synthetic resin of the polyvinyl type. Such material types are described in U.S. Pat. Nos. 2,286,215; 2,328,808; 2,322,085; 2,527,872; 2,541,474; 2,563,791; 2,768,154; 2,808,331; 2,852,382.

If desired a mixture of two or more of these colloids may be employed for dispersing the silver halide in its preparation.

The developing baths to be used in conjunction with the couplers of the invention are well-known to the man skilled in the art. They contain a developer of the p-phenylene diamine type, a development restrainer of the potassium bromide type, an antioxidant, such as sodium sulphite and an alkaline agent of the alkali hydrate or carbonate type. They may further contain both an antifoggant of the benzimidazole type and derivatives, of the benzothiazoles type and derivatives, of the triazole and tetrazole type and derivatives, such as mercapto-derivatives; and an anti-calcium substance of the alkaline phosphate and alkylendiaminoacetic acid type, such as for instance EDTA. Compounds known to the man skilled in the art, of the p-phenylene diamine type are those described for instance in U.S. Pat. Nos. 2,193,015; 2,656,273; 2,875,049 and in C. E. Kenneth Mees and T. H. James, *The Theory Of The Photographic Process*, third edition, table 13.4, pages 294–295.

Suitable developers, which can be employed to develop photographic elements, containing the couplers of the present invention, are the sulphites, the hydrochlorides and the sulphates of:

(a) N,N-diethyl-p-phenylene diamine;
(b) N-ethyl,N-β-methansulfonamido-ethyl-3-methyl-4-aminoaniline;
(c) N-ethyl,N-hydroxyethyl-2-methyl-p-phenylene diamine;
(d) N-ethyl,N-hydroxyethyl-p-phenylene diamine;
(e) N,N-diethyl-2-methyl-p-phenylene diamine.

The preparation of the couplers of the present invention will be described with particular reference to the step of attaching the heterocyclic nucleus of the present invention to the parent coupler bearing a chlorine atom as a substituent to the reactive methylene thereof. Parent couplers having or not halogen atoms attached to their reactive methylene have been described in the prior art (see U.S. Pat. Nos. 3,265,506 and 3,384,657).

EXAMPLE 1

Preparation of compound no. 6

60 g (0.1 M) of α-pivalyl-α-chloro-5-[γ-(2,4-ditert-amylphenoxy)-butyramido]-2-chloro-acetanilide, 11 g (0.106 M) of 3(5)-chloro-1,2,4-triazole, 400 ml of dry acetone and 11.9 g (0.22 M) of sodium methoxide were mixed and refluxed for one hour. The mixture was then poured into 800 ml of cold water and neutralized with conc. HCl. After three hours the solid product was filtered, washed with water, dried and recrystallized from 180 ml of methanol, thus obtaining 47 g (70% of the theoretical amount) of a white powder melting at 165°–167° C.

EXAMPLE 2

Preparation of compound no. 17

12.1 g of α-pivalyl-α-chloro-5-[γ-(2,4-ditert-amyl-phenoxy)-butyramido]-2-chloro-acetanilide, 3.1 g of 3(5)-methyl-sulphonyl-1,2,4-triazole, 250 ml of dibutyl-formamide and 2.3 g of finely powdered sodium hydroxide were mixed and the mixture was kept at room temperature for 6 hours with occasional shaking. 500 ml of water were then added thereto and dil. HCl was added up to a pH equal to 4÷5. The solid which separated was filtered, washed with water, dried and recrystallized from 100 ml of methanol, thus obtaining 10.2 g of a white crystalline product melting at 225°–227° C.

The compounds from 1 to 5, from 7 to 16 and the compounds 19, 20, 21, 22 were prepared in an analogous way as described in Example 1 but using the appropriate triazole instead of 3(5)-chloro-1,2,4-triazole and the appropriate parent coupler. Table 1 lists the triazoles used for each compound and references for their preparation. Compound 18 was prepared in an analogous way as described in Example 2 but using the appropriate parent coupler. Table 2 lists the molecular weight, the melting point and the solvent of crystallization and Table 3 the analytical data of the obtained compounds.

TABLE 1

| Compound no. | Heterocycle | Reference |
|---|---|---|
| 1 | 1,2,4-triazole | Merck-Schuchard |
| 2 | 1,2,4-triazole | Merck-Schuchard |
| 3 | Ethyl-1,2,4-triazole-3(5)-carboxylate | R.G. Jones, C. Ainsworth, J.Am.Chem.Soc. 77, 1539 |
| 4 | Isobutyl-1,2,4-triazole-3(5)-carboxylate | According to Jones, Ainsworth M.P. = 167°–169° C. |
| 5 21 | 2-ethyl-butyl-1,2,4-triazole-3(5)-carboxylate | According to Jones, Ainsworth M.P. = 122°–124° C. |
| 6 22 | 3(5)-chloro-1,2,4-triazole | Thiele, Manchot, Liebigs Ann. Chem. 303, 50 |
| 7 | 3(5)-bromo-1,2,4-triazole | Manchot, Noll, Liebigs Ann. Chem. 343, 9 |
| 8 | 3,5-dichloro-1,2,4-triazole | R. Stolle, W. Dietrich, J. |

TABLE 1-continued

| Compound no. | Heterocycle | Reference |
|---|---|---|
| | | pr, Chem. [2], 139, 203 (1934) |
| 9 | 3(5)-phenyl-1,2,4-triazole | H.G.O. Becker, J. pr. Chem. 311, 487 (1969) |
| 10 | 3(5)-methyl-1,2,4-triazole | R.G. Jones, C. Ainsworth, J.Am.Chem.Soc.,77, 1539 (1955) |
| 11 | 3(5)-methyl-5(3)-chlor-1,2,4-triazole | Thiele, Manchot, Liebigs Ann. Chem. 303, 42 |
| 12 | 3(5)-anilino-1,2,4-triazole | GB 1,157,256, 2 |
| 13 | 3(5)-(N-morpholine)-1,2,4-triazole | GB 1,157,256, 2 |
| 14 | 3(5)-ethoxy-5(3)-phenyl-1,2,4-triazole | H. Gehlen, G. Blankenstein, Liebigs Ann. Chem. 651, 139 |
| 15 | 3(5)-methylmercapto-1,2,4-triazole | C.F. Kroger, W. Sattler, H. Beyer, Liebigs Ann. Chem., 643, 131 |
| 16 | 3(5)-anilino-1,2,4-triazole | GB 1,157,286, 2 |
| 17 | 3(5)-methyl-sulfonyl-1,2,4-triazole | By Oxid. with $KMnO_4$ in $H_2O$ sol. of 3(5)-methylmercapto-1,2,4-triazole. M.P. = 214°–216° C. (ethanol) |
| 18 | 3(5)-methyl-sulfonyl-1,2,4-triazole | By Oxid. with $KMnO_4$ in $H_2O$ sol. of 3(5)-methylmercapto-1,2,4-triazole. M.P. = 214°–216° C. (ethanol) |
| 19 | 3(5)-methyl-5(3)-phenyl-1,2,4-triazole | H. Weidinger, J. Kranz, Ber. 96, 1068 (1963) |
| 20 | 3(5)-amino-1,2,4-triazole | GB 765,728, 2 |

TABLE 2

| Compound no. | Molecular weight | Solvent crystal | M.P. |
|---|---|---|---|
| 1 | 628.23 | Ethanol | 199°–201° C. |
| 2 | 680.315 | Methanol | 99°–101° C. |
| 3 | 710.320 | Ethanol | 201°–203° C. |
| 4 | 738.374 | Ethanol | 188°–190° C. |
| 5 | 766,428 | Methanol | 148°–150° C. |
| 6 | 672.704 | Methanol | 165°–167° C. |
| 7 | 717.158 | Methanol | 166°–168° C. |
| 8 | 707.149 | Heptane | 115°–118° C. |
| 9 | 714.357 | Methanol | 160°–162° C. |
| 10 | 652.283 | Ethanol | 186°–188° C. |
| 11 | 674.718 | Methanol | 168°–170° C. |
| 12 | 729.372 | Ethanol | 189°–192° C. |
| 13 | 723.366 | Heptane | 119°–121° C. |
| 14 | 758.411 | Cyclohexane | 96°–98° C. |
| 15 | 684.55 | Methanol | 146°–148° C. |
| 16 | 771.454 | Methanol | 89°–91° C. |
| 17 | 716.55 | Ethanol | 225°–227° C. |
| 18 | 758.430 | Methanol | 78°–83° C. |
| 19 | 728.382 | Methanol | 157°–159° C. |
| 20 | 653.272 | Methanol | 193°–195° C. |
| 21 | 483.40 | Diethyl-ether | 98°–100° C. |
| 22 | 746–420 | Methanol | 112°–114° C. |

TABLE 3

| Compound no. | Found | | | | | Calculated | | | | |
|---|---|---|---|---|---|---|---|---|---|---|
| | C % | H % | N % | Cl % | | C % | H % | N % | Cl % | |
| 1 | 65.87 | 7.60 | 11.01 | 5.53 | | 65.86 | 7.58 | 10.97 | 5.56 | |
| 2 | 67.21 | 8.04 | 10.20 | 5.26 | | 67.09 | 8.00 | 10.30 | 5.21 | |
| 3 | 64.12 | 7.43 | 9.84 | 5.05 | | 64.26 | 7.38 | 9.86 | 4.99 | |
| 4 | 65.21 | 7.62 | 9.43 | 4.88 | | 65.07 | 7.65 | 9.49 | 4.80 | |
| 5 | 66.07 | 7.92 | 9.18 | 4.63 | | 65.82 | 7.89 | 9.14 | 4.63 | |
| 6 | 62.50 | 7.06 | 10.22 | 10.47 | | 62.49 | 7.04 | 10.41 | 10.54 | |
| 7 | 58.62 | 6.57 | 9.68 | 5.01 | Br % = 11.11 | 58.62 | 6.61 | 9.77 | 4.94 | Br % = 11.15 |
| 8 | 59.84 | 6.61 | 9.80 | 14.86 | | 59.45 | 6.56 | 9.90 | 15.04 | |
| 9 | 68.98 | 7.39 | 9.77 | 4.99 | | 68.94 | 7.34 | 9.80 | 4.96 | |
| 10 | 66.28 | 7.78 | 10.02 | 5.48 | | 66.29 | 7.73 | 10.74 | 5.44 | |
| 11 | 62.65 | 7.32 | 10.24 | 10.33 | | 62.31 | 7.32 | 10.38 | 10.51 | |
| 12 | 66.99 | 7.21 | 11.32 | 4.87 | | 67.52 | 7.32 | 11.02 | 4.86 | |
| 13 | 64.25 | 7.61 | 11.52 | 4.96 | | 64.76 | 7.66 | 11.62 | 5.00 | |
| 14 | 68.12 | 7.45 | 9.26 | 4.69 | | 68.10 | 7.44 | 9.24 | 4.67 | |
| 15 | 63.25 | 7.36 | 10.28 | 5.20 | S % = 4.65 | 63.30 | 7.36 | 10.23 | 5.18 | S % = 4.69 |
| 16 | 68.44 | 7.69 | 10.89 | 4.59 | | 68.50 | 7.71 | 10.89 | 4.60 | |
| 17 | 60.04 | 6.96 | 9.55 | 5.03 | S % = 4.39 | 60.34 | 7.03 | 9.77 | 4.95 | S % = 4.48 |
| 18 | 61.79 | 7.44 | 9.28 | 4.70 | S % = 4.19 | 61.76 | 7.44 | 9.23 | 4.67 | S % = 4.23 |
| 19 | 69.46 | 7.53 | 9.58 | 4.89 | | 69.26 | 7.47 | 9.62 | 4.87 | |
| 20 | 64.22 | 7.54 | 12.65 | 5.47 | | 64.35 | 7.56 | 12.87 | 5.42 | |
| 21 | 54.83 | 5.81 | 11.51 | 14.53 | | 54.66 | 5.84 | 11.59 | 14.67 | |
| 22 | 61.15 | 7.54 | 9.34 | 4.81 | | 61.15 | 7.56 | 9.38 | 4.76 | |

EXAMPLE 3

Preparation of coupler No. 31.

202 g of α-pivalyl-α-chloro-5-[γ-(2,4-ditert-amyl-phenoxy)-butyramido]-2-chloro-acetanilide, 72 g of 6,8-dichloro-4-keto-benzotriazine, 35.3 g of triethylamine and 1,500 ml of dry acetone were mixed and refluxed for four hours. The mixture was poured into 3,000 ml of cold water and tretated with HCl to adjust the pH at 4÷5. After standing for few hours the solid was collected on a Buchner funnel, washed with water, dried and recrystallized from ethanol thus obtaining 199 g (75% of the theoretical amount) of a white product melting at 168°–170° C.

EXAMPLE 4

Preparation of coupler No. 37.

45 g of α-pivalyl-α-chloro-5-[γ-(2,4-ditert-amyl-phenoxy)-butyramido]-2-chloro-acetanilide, 13.5 g of 5-chloro-4-quinazolone, 500 ml of dry acetone and 8.9 g of sodium methoxide were mixed and refluxed for 1 hour. The mixture was then poured into 1,000 ml of cold water and acidified to pH 4÷5 with HCl under stirring. The solid was collected on a Buchner funnel, washed with cold water, air dried and recrystallized from ethanol thus obtaining 46 g (81% of the theoretical amount) of a white powder melting at 180°–182° C.

Compounds 23,25,27,29,30,32,36 and 41 were prepared in an analogous way as described in Example 3 but using a different 4-keto-benzotriazine compound and the appropriate parent coupler. Compounds 24,26,28,33,34,35,38,39,40,42,43,44, 45 were prepared in an analogous way as described in Example 4 but using a different quinazolone or pyrimidine-4-(3H)-one compound.

Table 4 lists the molecular weights, the solvent of crystallization and the melting points of the obtained compounds while Table 5 shows the analytical data thereof.

TABLE 4

| Compound no. | Molecular weight | solvent of cryst. | Melting point |
|---|---|---|---|
| 23 | 716.33 | Ethanol | 186°–188° C. |
| 24 | 715.343 | Ethanol | 197°–198° C. |
| 25 | 786.466 | Ethanol | 96°–98° C. |
| 26 | 632.816 | Ethanol | 171°–173° C. |
| 27 | 766.410 | Ethanol | 189°–191° C. |
| 28 | 665.282 | Ethanol | 190°–192° C. |
| 29 | 758.412 | Ethanol | 158°–160° C. |
| 30 | 794.46 | Methanol | 75°–77° C. |
| 31 | 785.232 | Ethanol | 168°–170° C. |
| 32 | 790.046 | Acetonitril | 62°–64° C. |
| 33 | 784.234 | Ethyl acetate | 215°–217° C. |
| 34 | 738.995 | Ethanol | 140°–141° C. |
| 35 | 915.224 | Ethanol | 136°–138° C. |
| 36 | 916-212 | Ethanol | 137°–139° C. |
| 37 | 749.788 | Methanol | 182°–184° C. |
| 38 | 819.921 | Methanol | 127°–129° C. |
| 39 | 819-921 | Methanol | 102°–104° C. |
| 40 | 799.503 | Ethanol | 125°–127° C. |
| 41 | 792-853 | Ethanol ethyl-acetate | 163°–165° C. |
| 42 | 864.377 | Acetonitril | 88°–90° C. |
| 43 | 787.405 | Ethanol | 197°–199° C. |
| 44 | 819.921 | Methanol | 109°–111° C. |
| 45 | 789.056 | Acetonitril + ligroin | 110°–112° C. |

TABLE 5

| Compound no. | Found C % | H % | N % | Cl % | | Calculated C % | H % | N % | Cl % | |
|---|---|---|---|---|---|---|---|---|---|---|
| 23 | 67.00 | 7.08 | 9.77 | 4.98 | | 67.07 | 7.04 | 9.78 | 4.95 | |
| 24 | 69.02 | 7.18 | 7.83 | 4.92 | | 68.84 | 7.19 | 7.83 | 4.96 | |
| 25 | 69.00 | 7.68 | 8.94 | 4.55 | | 68.72 | 7.69 | 8.91 | 4.51 | |
| 26 | 68.65 | 7.64 | 8.86 | — | | 68.33 | 7.65 | 8.85 | — | |
| 27 | 62.60 | 6.84 | 9.10 | 4.68 | S % = 4.13 | 62.69 | 6.84 | 9.14 | 4.63 | S % = 4.18 |
| 28 | 66.86 | 7.50 | 8.45 | 5.35 | | 66.80 | 7.42 | 8.42 | 5.33 | |
| 29 | 67.91 | 7.48 | 8.87 | 4.79 | | 68.10 | 7.44 | 9.24 | 4.67 | |
| 30 | 63.67 | 7.14 | 8.78 | 4.48 | S % = 4.08 | 63.50 | 7.10 | 8.82 | 4.46 | S % = 4.04 |
| 31 | 61.43 | 6.29 | 8.83 | 13.30 | | 61.18 | 6.16 | 8,92 | 13.55 | |
| 32 | 65.13 | 7.54 | 8.76 | — | S % = 3.99 | 65.37 | 7.53 | 8.87 | — | S % = 4.06 |
| 33 | 62.58 | 6.31 | 7.09 | 13.42 | | 62.79 | 6.30 | 7.14 | 13.56 | |
| 34 | 65.00 | 7.90 | 7.56 | — | S % = 4.30 | 65.01 | 7.91 | 7.58 | — | S % = 4.34 |
| 35 | 57.86 | 6.09 | 6.14 | 3.94 | Br % = 17.50 | 57.74 | 6.07 | 6.12 | 3.87 | Br % = 17.46 |
| 36 | 56.29 | 5.92 | 7.65 | 3.90 | Br % = 17.36 | 56.37 | 5.94 | 7.64 | 3.86 | Br % = 17.44 |
| 37 | 65.73 | 6.75 | 7.41 | 9.49 | | 65.68 | 6.72 | 7.47 | 9.46 | |
| 38 | 67.54 | 7.41 | 6.79 | 8.66 | | 67.39 | 7.38 | 6.83 | 8.65 | |
| 39 | 67.33 | 7.40 | 6.78 | 8.66 | | 67.39 | 7.38 | 6.83 | 8.65 | |
| 40 | 70.27 | 7.90 | 6.93 | 4.53 | | 70.61 | 7.94 | 7.01 | 4.44 | |
| 41 | 64.92 | 7.01 | 8.78 | 9.02 | | 65.14 | 6.99 | 8.83 | 8.94 | |
| 42 | 64.10 | 7.05 | 6.37 | 4.15 | Br % = 8.98 | 63.92 | 7.00 | 6.48 | 4.10 | Br % = 9.25 |
| 43 | 67.01 | 7.05 | 7.16 | 4.61 | | 67.12 | 7.04 | 7.12 | 4.50 | |
| 44 | 67.21 | 7.35 | 6.80 | 8.64 | | 67.39 | 7.38 | 6.83 | 8.65 | |
| 45 | 67.06 | 7.65 | 7.10 | — | S % = 4.07 | 66.98 | 7.66 | 7.10 | — | S % = 4.06 |

EXAMPLE 5

6 g of the couplers 2, 5, 6, 7, 8, 9, 10, 11, 13, 14, 15, 16 and 19 of the present invention and 6 g of the couplers A and B known in the prior art and having the following formula:

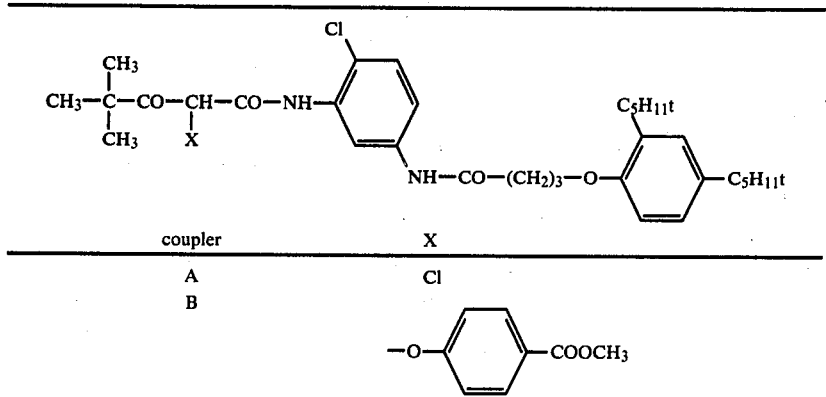

| coupler | X |
|---|---|
| A | Cl |
| B | —O—⌬—COOCH₃ | were dissolved in 10 ml of dibutylphthalate and 16 ml of ethyl acetate, emulsified with an aqueous solution of gelatin, mixed with a chloro-bromide photographic emulsion, coated on a transparent base and dried.

A part of each coating, containing 1.2 g of silver and 0.266.10$^{-3}$ Moles of coupler per square meter, was exposed and developed with a developer of the following composition (Developer A):

N-ethyl, N-$\beta$-methansulfonamido-ethyl-3-methyl-4-amino-aniline sulfate . . . 4 g
Benzyl alcohol . . . 3 g
Sodium sulfite, anhydrous . . . 2 g
Sodium carbonate, anhydrous . . . 60 g
Potassium bromide . . . 1 g
Water to make . . . 1,000 ml After a stop bath in a 2% acid acetic solution and bleach and fix processing, a yellow image was obtained whose sensitometric data are reported in Table 6. The speed data are referred to the coupler B chosen as control.

TABLE 6

| Compound no. | $D_{min}$ | $D_{max}$ | $\gamma(D = 0.9 \to 2.1)$ | Speed (D = 1) $-\Delta$ logE |
|---|---|---|---|---|
| 2 | 0.17 | 2.58 | 2.1 | +0.56 |
| 5 | 0.18 | 2.85 | 2.0 | +0.55 |
| 6 | 0.18 | 2.87 | 2.6 | +0.63 |
| 7 | 0.18 | 2.83 | 2.7 | +0.63 |
| 8 | 0.15 | 2.49 | 1.7 | +0.49 |
| 9 | 0.17 | 2.81 | 2.2 | +0.53 |
| 10 | 0.18 | 2.72 | 2.4 | +0.59 |
| 11 | 0.15 | 2.52 | 1.8 | +0.53 |
| 13 | 0.15 | 2.63 | 1.9 | +0.53 |
| 14 | 0.15 | 2.73 | 2.3 | +0.60 |
| 15 | 0.17 | 2.87 | 2.7 | +0.63 |
| 16 | 0.15 | 2.72 | 1.65 | +0.53 |
| 19 | 0.15 | 2.66 | 2.1 | +0.58 |
| A | 0.10 | 1.03 | — | −0.31 |
| B | 0.10 | 1.84 | 1.05 | 0 control |

EXAMPLE 6

Another part of each coating obtained as described in Example 5 was exposed and processed in an analogous way as described in Example 5 but developed with a developer of the following composition (Developer B):

2-amino-5-diethylamino-toluene chlorohydrate . . . 3 g
Sodium sulphite (anhydrous) . . . 4 g
Sodium carbonate (anhydrous) . . . 20 g
Potassium bromide . . . 2 g
Water to make . . . 1,000 ml A yellow dye image was thus obtained whose sensitometric data are reported in Table 7. The speed data are referred to the coupler B chosen as control.

TABLE 7

| Compound no. | $D_{min}$ | $D_{max}$ | $\gamma(D = 0.9 \to 2.1)$ | Speed (D = 1) $-\Delta$ logE |
|---|---|---|---|---|
| 2 | 0.16 | 2.62 | 2.8 | +0.17 |
| 5 | 0.16 | 2.98 | 2.8 | −0.03 |
| 6 | 0.18 | 2.93 | 3.7 | +0.15 |
| 7 | 0.18 | 2.98 | 3.8 | +0.13 |
| 8 | 0.17 | 2.71 | 2.5 | +0.01 |
| 9 | 0.17 | 2.85 | 2.8 | 0 |
| 10 | 0.16 | 2.84 | 3.5 | +0.11 |
| 11 | 0.15 | 2.79 | 3.0 | −0.05 |
| 13 | 0.18 | 2.80 | 3.4 | +0.08 |
| 14 | 0.18 | 2.90 | 3.7 | +0.13 |
| 15 | 0.18 | 2.84 | 3.7 | +0.13 |
| 16 | 0.11 | 2.94 | 2.5 | −0.08 |
| 19 | 0.16 | 2.87 | 3.6 | +0.08 |
| A | 0.11 | 2.23 | 1.35 | −0.32 |
| B | 0.11 | 2.76 | 2.4 | 0 control |

EXAMPLE 7

Another part of coatings obtained as described in Example 5 were incubated 7 days at 50° C. and 15% R.H. They were then exposed and processed in an analogous way as described in Examples 5 and 6 respectively using developers A and B. No difference was found between the results obtained with developers A and B. Table 8 shows the differences in sensitivity ($\Delta$S) and maximum densities ($\Delta D_{max}$) of incubated coatings with reference to the same non-incubated coatings of Example 5 developed with Developer A.

TABLE 8

| Compound no. | $\Delta S_{(D = 1)}(LogE)$ | $\Delta D_{max}$ |
|---|---|---|
| 2 | −0.05 | −0.5 |
| 5 | 0 | −0.3 |
| 6 | 0 | 0 |
| 7 | 0 | −0.3 |
| 8 | −0.05 | −0.8 |
| 9 | 0 | −0.2 |
| 10 | −0.02 | −0.5 |
| 11 | −0.02 | −0.4 |
| 13 | −0.04 | −0.2 |
| 14 | +0.02 | 0 |
| 15 | +0.02 | +0.2 |
| 16 | 0 | +0.2 |
| 19 | +0.02 | 0 |
| A | −0.02 | −0.6 |
| B | −0.05 | 0 |

EXAMPLE 8

A strip of each coating processed as described in Example 5 and 6 was exposed for 10 hours in a fadeometer with a Xenon lamp. The optical density variations, at D=1, of the exposed images were then calculated with respect to the original optical densities. The $\Delta D_{D=1}$ relative values are reported in Table 9. Said table also shows the optical density variations, at D=1, of the yellow images measured on other strips incubated for 24 hours at 90° C. and 70% of relative humidity.

TABLE 9

| | $\Delta D$ (D = 1) | | | |
|---|---|---|---|---|
| | 10 hours Xenon | | 24 hours 90° C., 70% R.H. | |
| Compound no. | Dev. A | Dev. B | Dev. A | Dev. B |
| 2 | −0.16 | −0.12 | +0.02 | +0.04 |
| 5 | −0.16 | −0.12 | 0 | +0.05 |
| 6 | −0.18 | −0.15 | 0 | −0.02 |
| 7 | −0.18 | −0.12 | 0 | 0 |
| 8 | −0.10 | −0.20 | 0 | −0.05 |
| 9 | −0.15 | −0.10 | 0 | 0 |
| 10 | −0.20 | −0.12 | −0.05 | −0.10 |
| 11 | −0.18 | −0.15 | +0.03 | 0 |
| 13 | −0.18 | −0.08 | 0 | 0 |
| 14 | −0.12 | −0.10 | 0 | 0 |
| 15 | −0.20 | −0.16 | −0.08 | 0 |
| 16 | −0.25 | −0.20 | −0.08 | 0 |
| 19 | −0.10 | −0.10 | −0.10 | −0.05 |
| A | −0.15 | −0.30 | 0 | −0.12 |
| B | −0.20 | −0.22 | −0.15 | 0 |

EXAMPLE 9

6 g of the couplers 25,30,31,32,35,36,38,39,40,44 and 45 of the present invention and 6 g of the couplers A and B known in the prior art and having the following structure:

A: α-pivalyl-α-chloro-5-[γ-(2,4-ditert-amyl-phenoxy)-butyramido]-2-chloro-acetanilide;

B: α-pivalyl-α-(4-carbomethoxy-phenoxy)-5-[γ-(2,4-ditertamylphenoxy)-butyramido]-2-chloro-acetamiline were dissolved in 10 ml of dibutyl-phthalate and 16 ml of ethylacetate, emulsified with an aqueous solution of gelatin, mixed with a chloro-bromide photographic emulsion, coated on a transparent base and dried.

A part of each coating, containing 1.5 g of silver and $0.266 \cdot 10^{-3}$ Moles of coupler per square meter, was exposed and developed with a developer of the following composition (Developer A):

N-ethyl-β-methane-sulfonamido-ethyl-3-methyl-4-amino-aniline sulfate . . . 4 g
Benzoyl alcohol . . . 3 g
Sodium sulfate, anhydrous . . . 2 g
Sodium carbonate, anhydrous . . . 60 g
Potassium bromide . . . 1 g
Water to make . . . 1,000 ml After a stop bath in a 2% acetic acid solution and a bleach and fix processing, a yellow image was obtained, whose sensitometric data are reported in Table 10. The speed data are referred to the coupler B chosen as a control.

TABLE 10

| Compound no. | $D_{min}$ | $D_{max}$ | γ (D = 0.8 → 2) | Speed (D = 1) − Δ logE |
|---|---|---|---|---|
| 25 | 0.09 | 2.64 | 1.8 | +0.35 |
| 30 | 0.12 | 2.83 | 2.4 | +0.58 |
| 31 | 0.12 | 2.65 | 1.75 | +0.36 |

TABLE 10-continued

| Compound no. | $D_{min}$ | $D_{max}$ | γ (D = 0.8 → 2) | Speed (D = 1) − Δ logE |
|---|---|---|---|---|
| 32 | 0.12 | 2.67 | 1.85 | +0.34 |
| 35 | 0.10 | 2.02 | 1.15 | +0.10 |
| 36 | 0.12 | 2.87 | 2.08 | +0.43 |
| 38 | 0.08 | 2.37 | 1.4 | +0.20 |
| 39 | 0.09 | 2.27 | 1.27 | +0.17 |
| 40 | 0.08 | 2.21 | 1.35 | +0.15 |
| 44 | 0.10 | 2.39 | 1.4 | +0.18 |
| 45 | 0.08 | 2.36 | 1.47 | +0.10 |
| B control | 0.09 | 2.11 | 1.22 | 0 |
| A | 0.07 | 1.07 | 0.65 | −1.1 |

EXAMPLE 10

Another part of each coating obtained as described in Example 9 was exposed and processed in an analogous way as described in Example 9 but developed with a developer of the following composition (Developer B):

2-amino-5-diethylamino-toluene chlorohydrate . . . 3 g
Sodium sulphite (anhydrous) . . . 4 g
Sodium carbonate (anhydrous) . . . 20 g
Potassium bromide . . . 2 g
Water to make . . . 1,000 ml A yellow dye image was thus obtained whose sensitometric data are reported in Table 11. The speed data are referred to the coupler B chosen as a control.

TABLE 11

| Compound no. | $D_{min}$ | $D_{max}$ | γ (D = 0.9 → 2.1) | Speed (D = 1) − Δ logE |
|---|---|---|---|---|
| 25 | 0.15 | 2.87 | 2.7 | +0.12 |
| 30 | 0.30 | 3.04 | 3.61 | +0.22 |
| 31 | 0.15 | 2.90 | 3.22 | +0.17 |
| 32 | 0.20 | 2.90 | 2.81 | +0.15 |
| 35 | 0.12 | 2.54 | 1.67 | −0.12 |
| 36 | 0.12 | 2.92 | 3.25 | +0.11 |
| 38 | 0.16 | 2.88 | 2.1 | +0.03 |
| 39 | 0.15 | 2.84 | 1.76 | +0.11 |
| 40 | 0.12 | 2.85 | 2.1 | +0.04 |
| 44 | 0.15 | 2.88 | 2.1 | +0.04 |
| 45 | 0.15 | 2.98 | 2.5 | +0.03 |
| B control | 0.12 | 2.89 | 2.04 | 0 |
| A | 0.12 | 2.09 | 1.07 | −0.45 |

EXAMPLE 11

Another part of coatings obtained as described in Example 9 were incubated 7 days at 50° C. and 15% R.H. They were then exposed and processed in an analogous way as described in Examples 9 and 10, respectively using developers A and B. No difference was found between the results obtained with developers A and B. Table 12 shows the difference in sensitivity (ΔS), minimum densities ($\Delta D_{min}$) and maximum densities ($\Delta D_{max}$) of the incubated coatings with reference to the same non-incubated coatings of Example 9 developed with developer A.

TABLE 12

| Compound no. | ΔS logE | $\Delta D_{min}$ | $\Delta D_{max}$ |
|---|---|---|---|
| 25 | +0.02 | +0.01 | 0 |
| 30 | +0.02 | +0.02 | −0.05 |
| 31 | +0.03 | 0 | +0.05 |
| 32 | +0.03 | +0.03 | +0.05 |
| 35 | 0 | 0 | 0 |
| 36 | +0.03 | +0.02 | 0 |
| 38 | +0.03 | +0.01 | 0 |
| 39 | +0.02 | 0 | 0 |

TABLE 12-continued

| Compound no. | ΔS logE | ΔD$_{min}$ | ΔD$_{max}$ |
|---|---|---|---|
| 40 | +0.03 | +0.01 | 0 |
| 44 | +0.03 | +0.01 | 0 |
| 45 | +0.02 | +0.02 | +0.10 |
| B control | +0.01 | +0.01 | +0.05 |
| A | +0.03 | 0 | 0 |

EXAMPLE 12

A strip of each coating processed as described in Examples 9 and 10 was exposed for 10 hours in a fadeometer at a Xenon lamp. The optical density variations, at D=1, of the exposed images were then calculated with respect to the original optical densities. The ΔD$_{D=1}$ relative values are reported in Table 13. Said table also shows the optical density variations, at D=1, of the yellow images, measured on other strips incubated for 24 hours at 90° C. and 70% R.H.

TABLE 13

| Compound no. | 10 hours Xenon | | 24 hours 90° C. 70% R.H. | |
|---|---|---|---|---|
| | Dev. A | Dev. B | Dev. A | Dev. B |
| 25 | −0.05 | −0.06 | 0 | 0 |
| 30 | −0.12 | −0.10 | 0 | −0.04 |
| 31 | −0.10 | −0.10 | 0 | 0 |
| 32 | −0.12 | −0.10 | 0 | 0 |
| 35 | −0.07 | −0.08 | +0.05 | 0 |
| 36 | −0.12 | −0.12 | −0.04 | +0.08 |
| 38 | −0.10 | −0.12 | +0.05 | 0 |
| 39 | −0.12 | −0.08 | 0 | +0.04 |
| 40 | −0.04 | −0.03 | −0.04 | 0 |
| 44 | −0.06 | −0.05 | −0.05 | 0 |
| 45 | −0.10 | −0.10 | 0 | 0 |
| B | −0.20 | −0.20 | −0.14 | −0.20 |
| A | −0.10 | −0.24 | +0.03 | −0.03 |

I claim:

1. A multilayer color photographic element including a base and at least one silver halide emulsion layer characterized by having at least one two-equivalent pivalylacetanilide coupler having attached to the reactive methylene thereof a 5-membered heterocyclic nucleus, said nucleus bonded to said methylene from a nitrogen atom in the 1-position on said heterocyclic nucleus, said 5-membered nucleus having nitrogen atoms in the 2- and 4-positions respectively bonded by double bonds to carbon atoms in the 3- and 5-positions, said at least one coupler being in reactive association with the silver halide of said at least one silver halide emulsion.

2. A photographic element according to claim 1 characterized by having said at least one coupler dissolved in a substantially water-immiscible organic solvent dispersed in said at least one silver halide emulsion layer.

3. A photographic element according to claim 2 wherein said at least one coupler is further characterized by having at least one substituent attached to the phenyl nucleus of the acetanilide moiety thereof selected from the class consisting of halogen, alkyl, carboxy and sulphoxy directly attached to said phenyl nucleus or attached through amine, carbonyl, alkylene, oxygen, sulphur, or phenyl groups.

4. A photographic element according to claim 3 wherein said at least one coupler is characterized by having, attached to the phenyl nucleus of the acetanilide moiety thereof, a substituent selected from the class consisting of halogen and alkyl groups directly attached to said phenyl nucleus or attached to said phenyl nucleus through amine, carbonyl, oxygen, sulphur, or phenyl groups.

5. A photographic element according to claim 4 further characterized by having, attached to the aniline moiety thereof or the 5-membered heterocyclic nucleus, alkyl groups having a total of from 10 to 25 carbon atoms.

6. A photographic element according to claim 1 wherein said at least one coupler is further characterized by having attached to the reactive methylene as said 5-membered heterocyclic a 1,2,4-triazole group as a splitting off nucleus, and by having attached to the 3-position of said five-membered heterocyclic nucleus a substituent selected from the class consisting of halogen, carboxy acid ester, phenyl, alkyl, phenylamino, 4-nitrogen containing heterocyclic, alkylthio, alkylsulfoxy, and amino groups.

7. A photographic element according to claim 1 wherein said at least one coupler is further characterized by said splitting off heterocyclic nucleus being represented by the formulae:

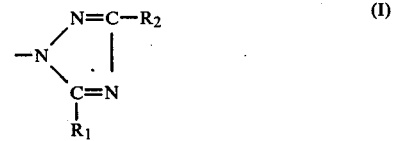

(I)

wherein R$_1$ and R$_2$ each represent a hydrogen atom or a substituent chosen within the class of halogen; a carboxy acid ester whose alkyl chain has from 1 to 18 carbon atoms; an amino group; a nitrogen containing heterocyclic nucleus attached through said nitrogen atom; an alkyl group having from 1 to 18 carbon atoms; an alkylthio or alkoxy group having from 1 to 18 carbon atoms; an alkylsulphoxy group having from 1 to 18 carbon atoms; a carboxy acid group; a sulphoxy acid group; a non substituted phenyl group or a phenyl group substituted with substituents chosen from the class consisting of halogen, alkyl having from 1 to 18 carbon atoms; carboxy acid ester whose alkyl chain contains from 1 to 18 carbon atoms, cyano, an alkoxy group having from 1 to 18 carbon atoms, and a sulphoxy acid group.

8. The photographic element of claim 1 wherein said 5-membered heterocyclic nucleus attached to the reactive methylene is 1,2,4-triazole.

* * * * *